(12) United States Patent
Misczynski et al.

(10) Patent No.: US 7,164,941 B2
(45) Date of Patent: Jan. 16, 2007

(54) METHOD AND SYSTEM FOR CONTACTLESS MONITORING AND EVALUATION OF SLEEP STATES OF A USER

(76) Inventors: Dale Julian Misczynski, 1800 Barton Creek Blvd., Austin, TX (US) 78735-1606; Vladislav Bukhman, 419 First St., East Northport, NY (US) 11731

( * ) Notice: Subject to any disclaimer, the term of this patent is extended or adjusted under 35 U.S.C. 154(b) by 201 days.

(21) Appl. No.: 11/020,784

(22) Filed: Dec. 22, 2004

(65) Prior Publication Data

US 2005/0148893 A1    Jul. 7, 2005

Related U.S. Application Data

(60) Provisional application No. 60/534,569, filed on Jan. 6, 2004.

(51) Int. Cl.
*A61B 5/05* (2006.01)

(52) U.S. Cl. .................................... 600/513

(58) Field of Classification Search ............... 600/9, 600/13, 407, 411, 421, 422, 481, 483, 513
See application file for complete search history.

(56) References Cited

U.S. PATENT DOCUMENTS

| 6,238,333 B1 * | 5/2001 | Loos ........................... 600/9 |
| 6,535,625 B1 * | 3/2003 | Chang et al. ............... 382/128 |
| 2005/0124846 A1 * | 6/2005 | Pasula et al. ................. 600/9 |

\* cited by examiner

*Primary Examiner*—Robert Pezzuto
*Assistant Examiner*—Yun Haeng Lee

(57) ABSTRACT

The invention relates to a method and device for contactless monitoring and evaluation of sleep states of a user. The invention comprises a seamless continuous evaluation of cardiac activity variability and uses these data as an input for evaluation and quantitative assessment of sympathetic and parasympathetic activity of autonomic nervous system, which are reliable markers of physiological condition of a user. The device is embedded within two thin mattress pad layers, eliminating any direct contact between electrodes and a user's body. The invention enables remote monitoring and evaluation of sleep states without involvement of trained professionals.

20 Claims, 10 Drawing Sheets

US 7,164,941 B2

METHOD AND SYSTEM FOR CONTACTLESS MONITORING AND EVALUATION OF SLEEP STATES OF A USER

CROSS REFERENCE TO RELATED APPLICATIONS

This patent application is based upon Provisional Patent Application Ser. No. 60/534,569 filed on Jan. 6, 2004

BACKGROUND OF THE INVENTION

The present invention relates to the field of sleep monitoring in particular to the monitoring and evaluation of sleep states of a user.

Obstructive sleep apnea is a serious disorder caused by an obstruction of the upper airway during sleep, which affects around 20 million Americans. According to the National Commission on Sleep Disorders Research the vast majority of patients with sleep disorders currently remain undiagnosed.

Under normal circumstances an individual progresses through an orderly succession of sleep states and stages. The first cycle begins by going from wakefulness to Non-Rapid Eye Movement (NREM) sleep. NREM sleep is followed by Rapid Eye Movement (REM) sleep, and the two sleep states alternate throughout the night with an average period of about 90 minutes. A night of a normal human sleep usually consists of 4–6 NREM/REM sleep cycles.

To facilitate the diagnosis of sleep disorder, patients are monitored using polygraph recording of electroencephalograms (EEG), Electrocardiograms (ECG), electro-oculogram (EOG), and other data.

Very often sleep evaluation is not possible without the use of sedative drugs because the plurality of electrodes connected to the patient inflicts anxiety and restrains the patient from a normal sleeping pattern. In these cases the validity of results are downgraded significantly.

The equipment used for sleep monitoring is costly and normally requires trained professionals for analysis and interpretation. Sleep monitoring usually is provided in specialized facilities in a hospital environment.

The present invention enables true tele-medicine sleep monitoring applications. This is not currently practical since the current state of the art is confined to hospitals or acute care facilities.

SUMMARY OF THE INVENTION

Figure 1:
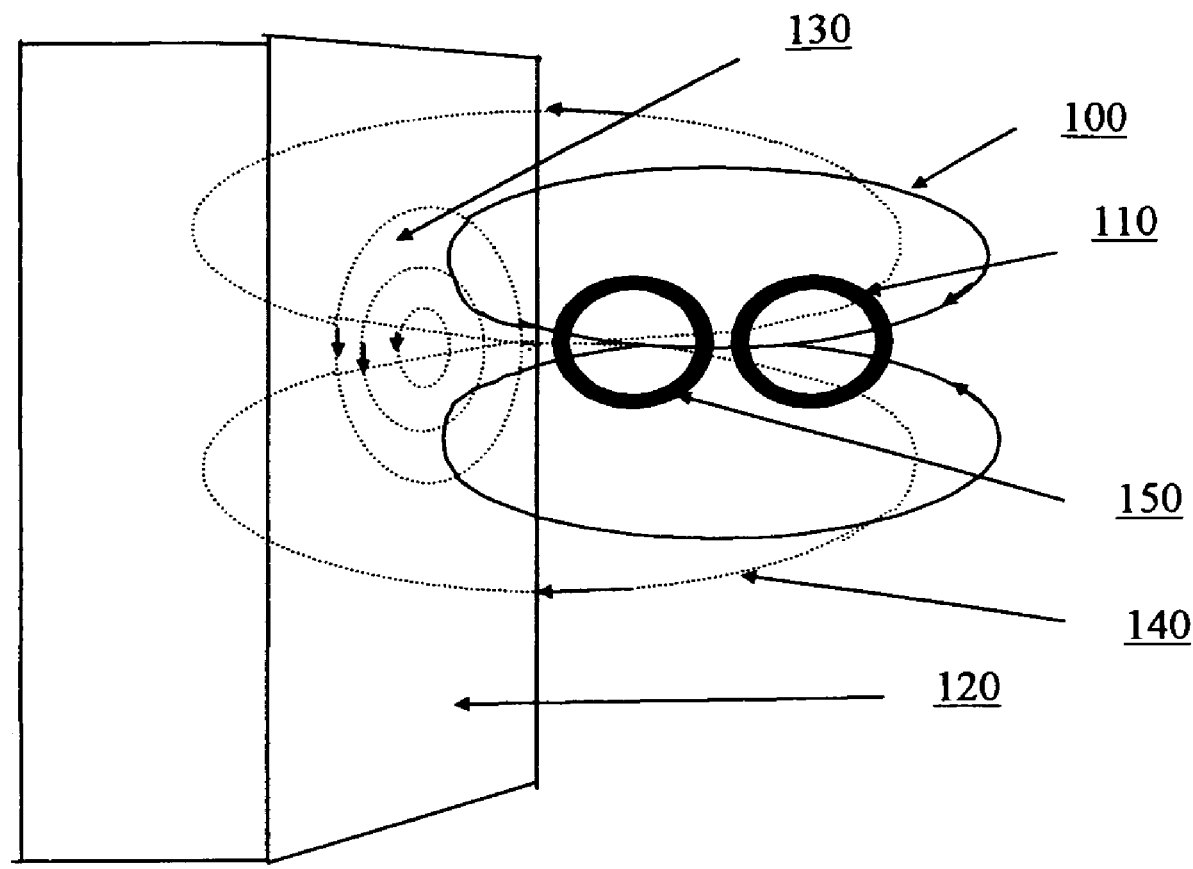
FIG. 1 shows the contactless sleep evaluation device made in a form of a small mattress pad.

In the following description, numerous specific details are set forth to provide a thorough understanding of the present invention. However, it will be obvious to those skilled in the art that the present invention may be practiced without such specific details. For the most part, details concerning specific non-essential materials and the like have been omitted inasmuch as such details are not necessary to obtain a complete understanding of the present invention and are within the skills of persons of ordinary skill in the relevant art.

The fundamental aspect of the invention is the real-time contactless monitoring and evaluation of the sleep states of the user incorporated in a portable contactless device embedded in the bed of the user.

These objectives are reached by monitoring cardiac activity variability, where cardiac activity signals are derived from an electromagnetic inductance device without electrodes contacted to the body of the user.

Cardiac activity is mainly conditioned by heart rate and stroke volume. Heart rate is defined as a number of beats per minute, while stroke volume is defined as the volume of blood in milliliters (ml) ejected from the heart due to contractions of the left ventricular.

In the present disclosure, cardiac activity (CA) is defined as a cumulative index in normalized units of the stroke volume (SV) and the heart rate (HR).

Heart rate and stroke volume are not the same for each cardiac cycle (beat). The rate and volume vary from beat to beat. This fluctuation is controlled by sympathetic and parasympathetic branches of the autonomic nervous system (ANS) and reflects the individual's capacity to adapt effectively to environmental demands. The parasympathetic and sympathetic divisions of the ANS constantly cooperate, either facilitating or inhibiting cardiovascular functions. There is a direct correlation between the variability of heart rate and stroke volume and the activity of parasympathetic and sympathetic systems.

During the transition from wakefulness to sleep, and going through sleep stages, dramatic changes occur in the functions of the sympathetic and parasympathetic systems. It has been shown in many studies, that during the transition from wakefulness to sleep, sympathetic activity decreases from 53±9% of total power to 41±5%, while parasympathetic activity markedly increases from 19±4% to 40±6%. During REM sleep sympathetic activity does not change, while the parasympathetic activity decreases by 17±2%.

One of the objectives of the present invention is to provide quantitative assessment of sympathetic and parasympathetic activity and the changes in sympathetic and parasympathetic activity overtime by analyzing cardiac activity variability (CAV). This data is used to discriminate wakefulness state, and sleep stages of the user.

This is a two-step process. The first step includes acquisition of signals representing continuous beat-to-beat changes of stroke volume and heart rate and the translation of the data in to meaningful values.

The second step includes the detection, discrimination, and quantitative evaluation of the "fingerprints" of sympathetic and parasympathetic activities by analyzing the variability of cardiac activity.

In the present invention, a Fast Fourier Transform (FFT) is used for the mathematical transformation of cardiac activity variability data into power spectral density to discriminate and quantify sympathetic and parasympathetic activities. This information is used as an input for discrimination of wakefulness and sleep states of the user.

In the final aspect of the present invention an electromagnetic inductance signal-processing device is disclosed. The signal-processing device comprises excitation and sensor coils, lock-in amplifier, power and ancillary amplifiers, a processor, and memory. The processor controls the lock-in amplifier, performs all tasks associated with spectral density power (SDP) and signal analysis, and runs the FFT, service and display programs. The device also includes memory for storing all intermediate data before or after submitting them to the processing, log files, and time-stamped sleep states records.

DETAILED DESCRIPTION OF THE DRAWINGS

The thoracic electromagnetic inductance technology is based on evaluation of cardiac activity by the measurement of fluctuation of eddy current induced in the heart region using an alternating current induced magnetic field. This technology has been used for decades in non-destructive defect control, geophysics, for content measurements and etc. Starting in 1965, this technology has been successfully used in medical applications. Main advantages of magnetic inductance method include:
- absence of physical contacts between the body and magnetic inductance device sensors;
- there is a measured improvement in signal to noise compared to methods using contact sensors;
- a seamless induction of probe current to the body without the screening effect of an insulation layer (clothing) and bones.

FIG. 1 illustrates the basic principles of the thoracic electromagnetic inductance technology. Electromagnetic field 100 of excitation coil 110 induces current in the conductive body 120 proportionally to the conductivity distribution. Currents in the body induce the secondary magnetic field 130 which induce 140 current in a receiver coil 150, sensor. Operation of the sensor is based on measuring changes in the amplitude of a marginal RF oscillator, caused by eddy current losses in the heart region. Changes of amplitude reflect changes in heart region energy absorption, which depends on the volume of blood in the heart and heart rate.

Validity studies and clinical trials demonstrated 0 bias between measurements made using electromagnetic inductance technology and measurements performed by invasive and non-invasive medical devices used in clinical practice.

Figure 2:
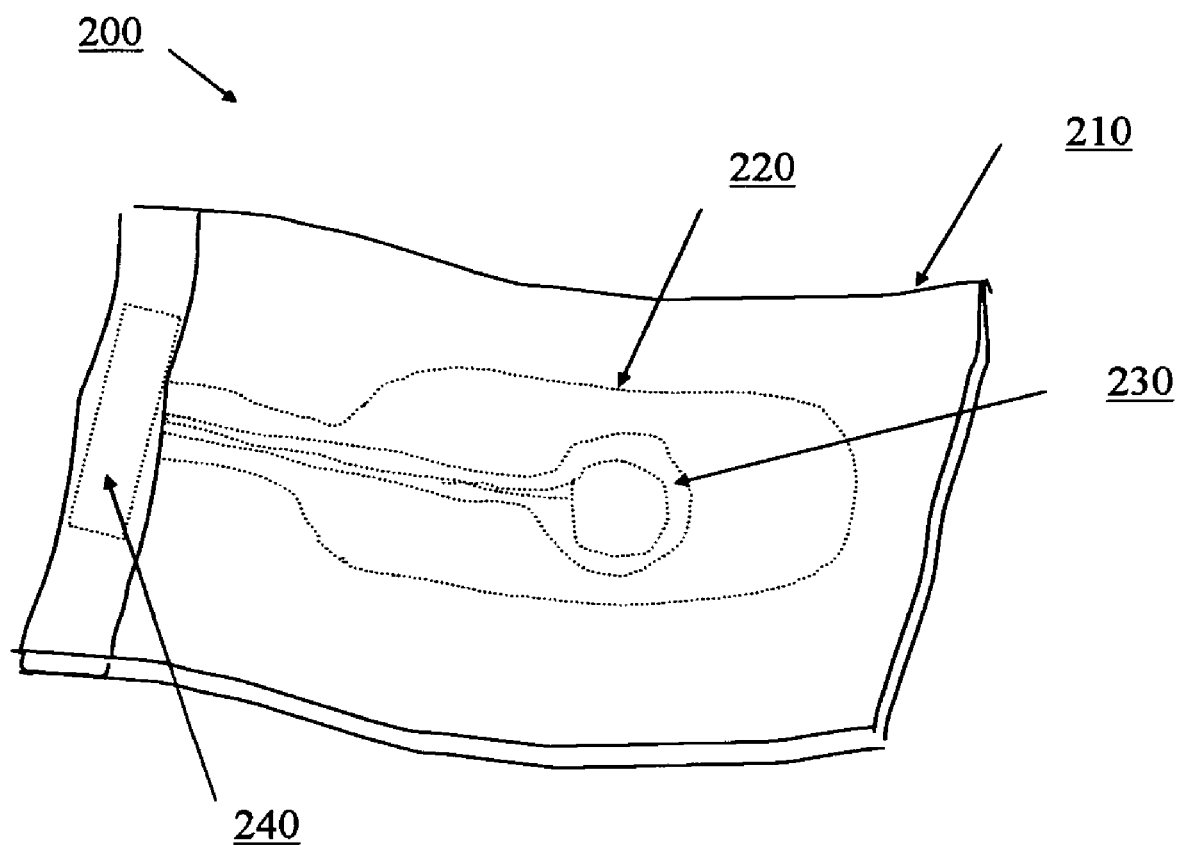
FIG. 2 illustrates the basic principals of the electromagnetic inductance method.

FIG. 2 shows the exemplary electromagnetic inductance device 200 incorporated in two layers of a small mattress pad 210. The large size of the excitation coil 220 induces a strong and relatively uniform induction field thus providing an improved resolution for sensing coils 230. Instead of wire wound around a core, these flexible sensors use metal lines (or traces) deposited on a flexible plastic-like material, similar to a flexible printed circuit board. Such flexible plastic substrates are produced by GE for inspection devices based on eddy current principals. The mattress pad with inserted coils is designed for multiple usages and is washable. The processing unit 240 is attached to the edge of the mattress pad using, for example, a standard RS232 (DB9) connector.

Figure 3A:
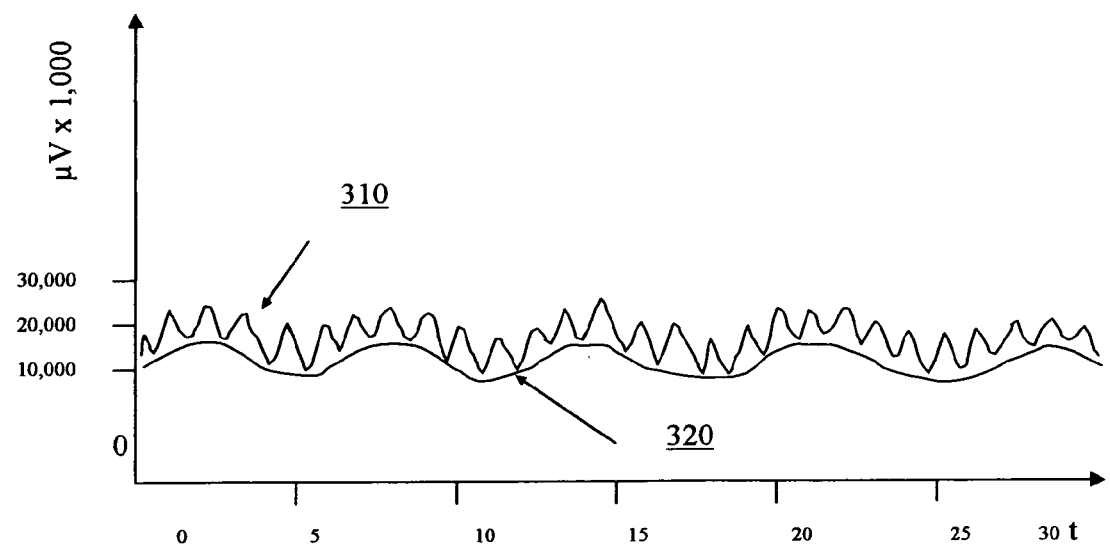
FIG. 3a shows an example of a waveform reflecting changes of cardiac activity recorded by sleep monitoring device.

FIG. 3a shows a 30 second sample of CA waveforms 310 performed by a sleep monitoring device using electromagnetic inductance technology. Respiratory component 320 affects the waveform. The respiratory component 320 is built by cubic spline approximation methods using minimum points of the waveform 310.

Figure 3B:
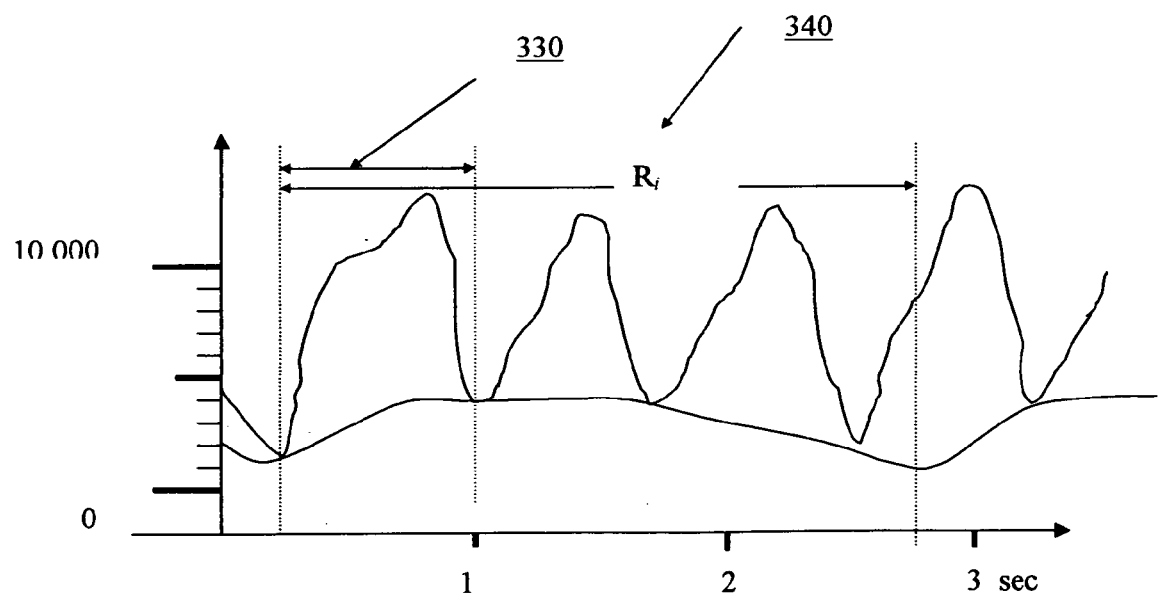
FIG. 3b shows a 3 second fragment of changes of cardiac activity.

FIG. 3b shows a 3 second fragment of CA waveform. An interval 330 reflects the cardiac cycle and an interval 340 reflects respiratory rate. Respiratory rate is defined as:

$$RR_i = \frac{60}{R_i}$$

Where:
$RR_i$=respiratory rate in breat/min;
$R_i$=width of respiratory wave in sec.

Figure 4A:
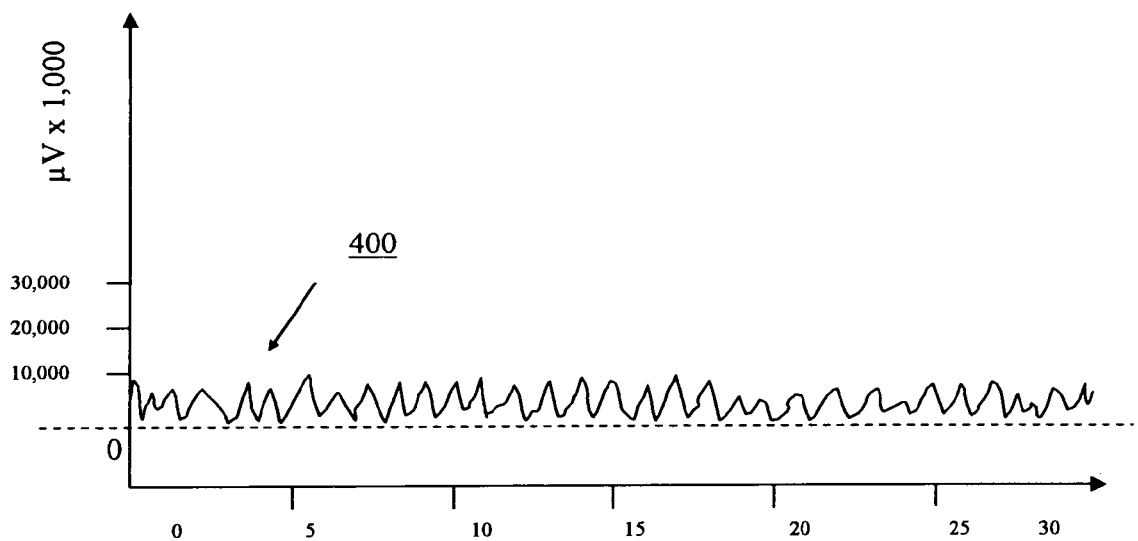
FIG. 4a shows an example of cardiac activity waveform without respiratory artifacts.

FIG. 4a illustrates the 30 seconds CA waveform 400 with respiratory artifacts removed.

Figure 4B:
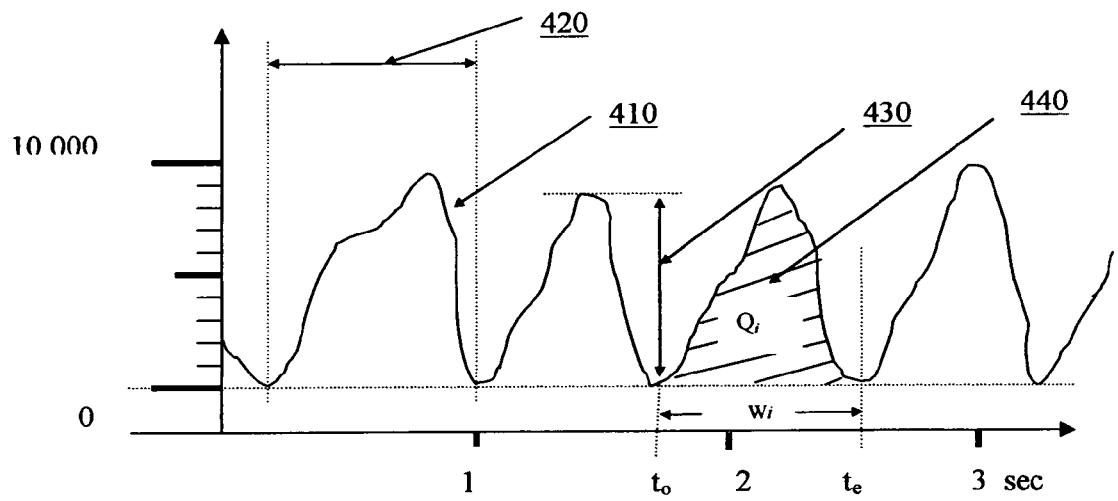
FIG. 4b shows a 3 second fragment of changes of cardiac activity without respiratory artifacts.

FIG. 4b illustrates 3 seconds fragment 410 of CA waveforms with respiratory artifacts removed.

Width of CA wave 420 reflects the cardiac cycle that is defined as:

$$HR_i = \frac{60}{W_i} * 1000$$

Where:
$HR_i$=heart rate of cardiac cycle i in beat/min;
$W_i$=width of wave i in ms.

Magnitude 430 of the wave reflects the stroke volume, while the area below the wave 440 represents the cumulative CA index. Area $Q_i$ can be determined by using equation:

$$Q_i = \int_a^b f(x)\,dx \qquad (1)$$

Where:
$a=t_o$;
$b=t_e$

Because of the discrete nature of analyzed signals, the area $Q_i$ of each CA wave 440 is calculated using equation (2), which is a discrete representation of equation (1).

$$Q_i = \sum_{j=1}^n A_j \qquad (2)$$

Where:
$Q_i$=area of CA wave related to cardiac cycle i,
$A_j$=amplitude of sample j of CA wave of cardiac cycle i,
n=number of samples within cardiac cycle i.

The sampling rate used in the present invention is 128 Hz because sampling in a range of 100 to 250 provides sufficient sensitivity and reproducibility. However, persons of ordinary skill in the art may successfully use other values.

The $CA_i$ is equal:

$$CA_i = k * Q_i n.u. \qquad (3)$$

Where:
k is a normalizing factor for converting calculated value of $Q_i$ in the meaningful value;
$Q_i$=area of wave $W_i$;
n.u. stands for normalized unit.

The measurement of real values of SV and HR is outside the scope of the present invention, because the evaluation and discrimination of user's sleep state is based on the CA variability (CAV), which is a cumulative derivative of SV and HR, rather then on SV and HR per se. For this reason factor k is arbitrary and in the present invention k is equal to 0.01.

Figure 5A:
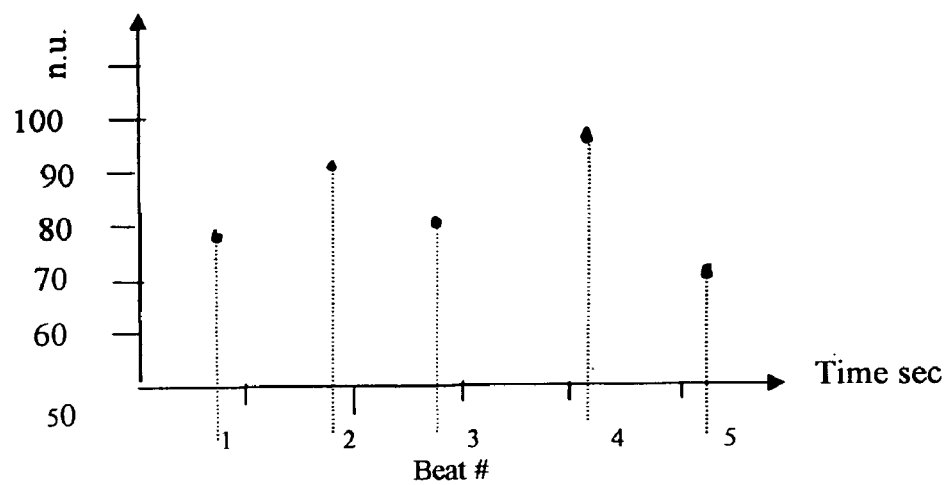
FIGS. 5a–5c illustrates time-domain distribution of cardiac activity measured data.

FIG. 5a shows an example of the distribution plot of measured CA of 5 consecutive cardiac cycles (beats). Due to time fluctuation between cardiac cycles, the plot represents irregular time-sampling signals.

Figure 5B:
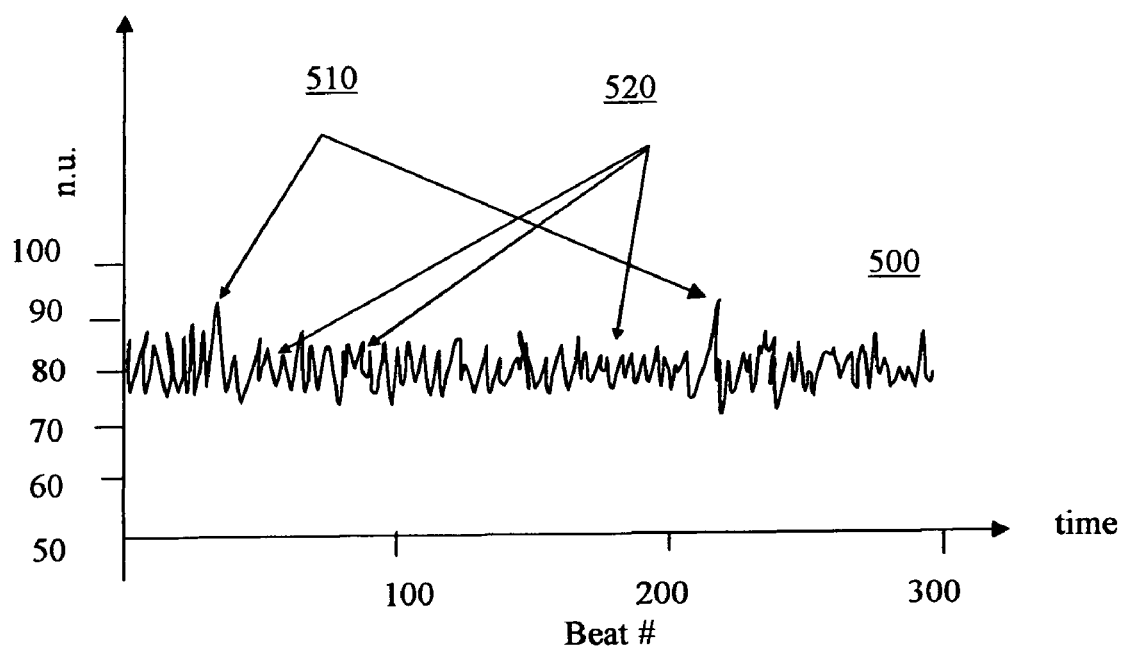

FIG. 5b shows an irregular sampled plot (tachogram) 500 of 300 consecutive $CA_i$ values. The ordinate represents measured values of $CA_i$ Spikes 510 are due to increased sympathetic activity, while low fluctuations area 520 represents points on prevalence of parasympathetic activity.

Traditional spectral analysis methods are not able to process irregular sampled signals. In the present invention the irregular sampled tachogram is resampled using a sampling rate equal to half of the average interval found in the time-domain tachogram. This rate is compliant with Nyquist theorem (i.e. sampling rate is higher than twice the highest frequency contained in the signal) and at the same time it is low enough for effective usage of processing power. However, persons of ordinary skill in the art may successfully use other values.

Figure 5C:
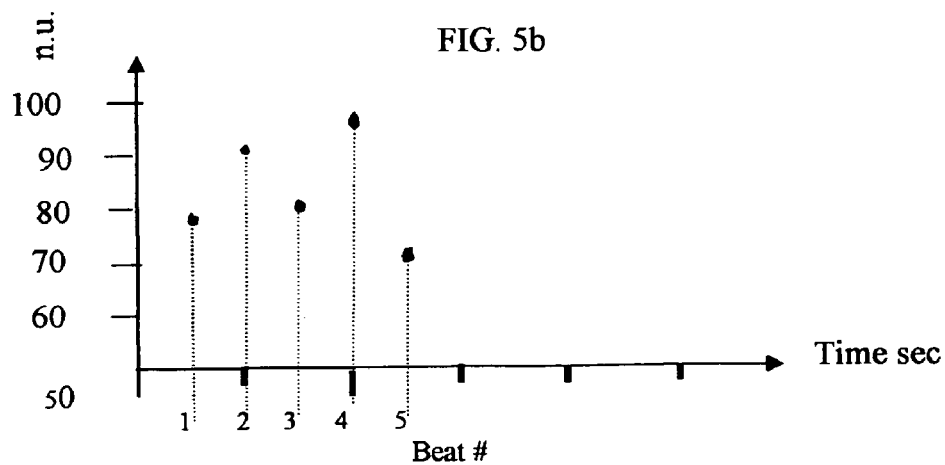

FIG. 5c shows an example of resampling of the tachogram shown on FIG. 5a. Resampled points are repositioned at the new sampling interval equal to the half average interval found in the tachogram shown on FIG. 5a.

The resampled tachogram is used as an input for the Fourier Transform spectral analysis.

Figure 6A:
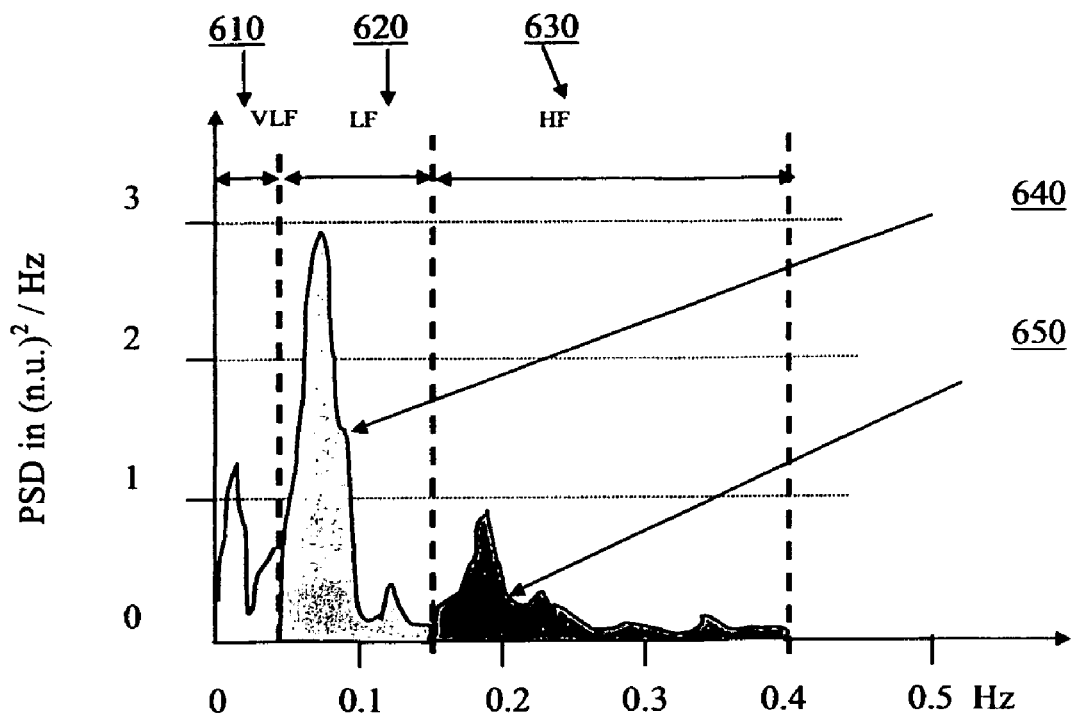
FIGS. 6a–6b demonstrates three main spectral components of the variability of the cardiac activity.
Figure 6B:
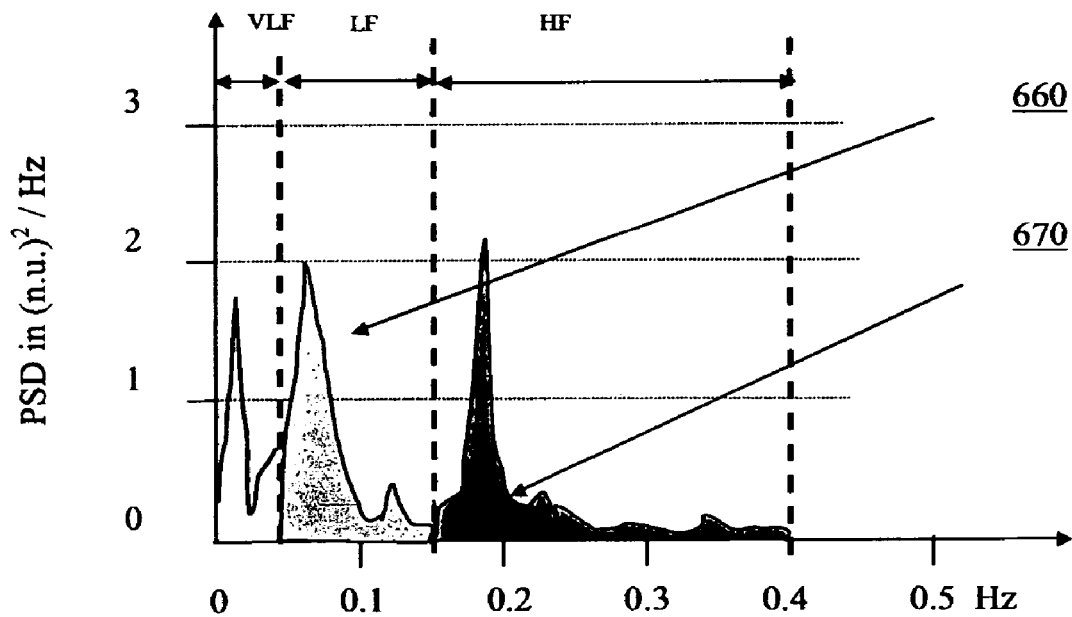

The total power spectrum of CAV resampled tachogram is divided into three main frequencies, FIGS. 6a–6b:

the very low frequency range (VLF) 0.0033 to 0.04 Hz, discriminates slower changes in CAV and reflects sympathetic activity 610;
low frequency range (LF) 0.04 to 0.15 Hz representing both sympathetic and parasympathetic activity 620;
and high frequency (HF) 0.15 to 0.4 discriminates quicker changes in the CA and reflecting parasympathetic activity 630.

The power spectrum division on 0.0033 to 0.04, 0.04 to 0.15, and 0.15 to 0.4 is defined by a standard developed by *Task Force of European Society of Cardiology and North American Society of Pacing and Electrophysiology, European Heart Journal* (1966), 17, 354–381.

In the present invention, the Fast Fourier Transform (FFT) algorithm is applied to evaluate the discrete-time Fourier transform (DFT) of N equispaced samples of a 5 minutes time-series of records of CAV. A five-minute time series is recommended by the standard developed by *Task Force of European Society of Cardiology and North American Society of Pacing and Electrophysiology, European Heart Journal* (1966), 17, 354–38. However, persons of ordinary skill in the art may successfully use other values.

The number of operations required to calculate the FFT is proportional to $\log_2 N$ when N is an integer power of 2. In the present invention N=1024 and covers the maximum possible number of samples of 5 minutes of the time series. The number of samples is artificially increased by adding zero-value samples (zero-padding), if the number of samples is less than 1024.

Standard, off-the-shelf FFT software is used for calculation of the total spectrum power (TP), power spectrum distribution, and calculation of sympathetic and parasympathetic spectral powers, e.g. FFTW Version 3.0.1, Matlab, The Mathworks. However, persons of ordinary skill in the art may successfully use other FFT software.

FIG. 6a illustrates an example of calculated distribution of power spectrum density (PSD) 640 and 650 for a person in wakefulness state.

FIG. 6b shows an example of calculated power spectrum distribution 660 and 670 when a person is in the NREM sleep state. The transition from wakefulness to NREM sleep is marked by a progressive decrease in LF spectrum power reflecting sympathetic activity and a significant increase in HF spectrum power reflecting parasympathetic activity.

Figure 7:
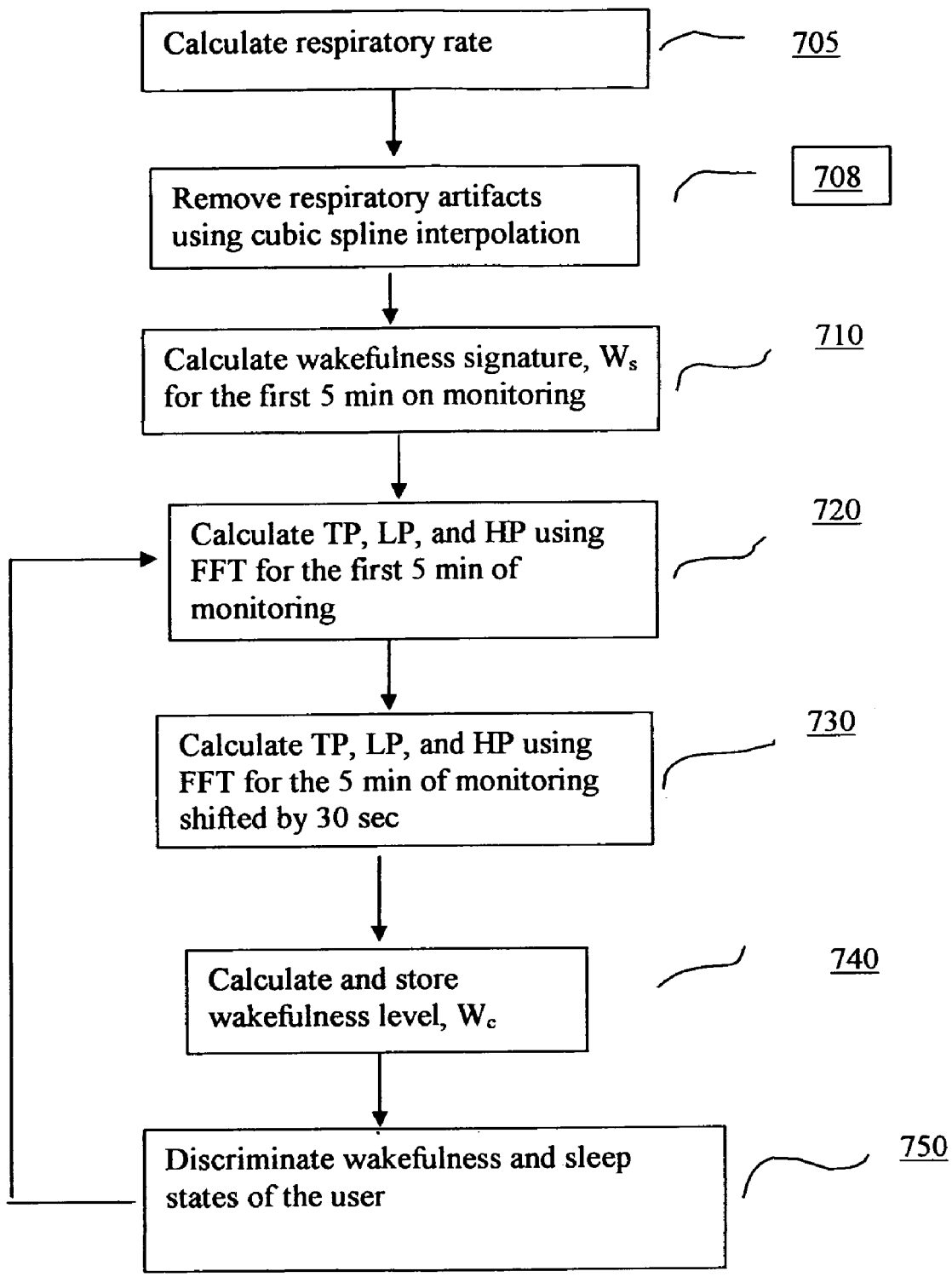
FIG. 7 illustrates steps of sleep evaluation.

FIG. 7 illustrates steps of evaluation and decimation of wakefulness and transition to the sleep state of the user.

The first step 705 the respiratory rate, RR is calculated, time stamped, and stored in patient's sleep states journal.

After the respiratory rate is calculated, the respiratory artifacts are removed 708 using cubic spline interpolation.

In step 710, total power (TP), LF activity power (LP), and HF activity power (HP) are calculated for the first 5 minutes of monitoring using FFT algorithm.

The second step 720, wakefulness signature level $W_s$ is calculated as ratio of LP to HP.

$$W_s = \frac{LP_s}{HP_s} \qquad (4)$$

Where:
$W_s$=wakefulness signature value,
$LP_s$=signature sympathetic activity power,
$HP_s$=signature parasympathetic activity power.

Next step, 5 minutes time interval is shifted by 30 seconds and the new set of $TP_c$, $LP_c$ and $HP_c$ is calculated 730.

In step 740 the current wakefulness level $W_c$ is calculated:

$$W_c = \frac{LP_c}{HP_c}$$

The calculated value $W_c$ is stored in FIFO buffer. The buffer contains data of 5 minutes of monitoring.

The transition from wakefulness to NREM sleep is characterized by the rapid shift of predominance of sympathetic activity to predominance of parasympathetic activity. Sympathetic power, LP drops up to 10%, while parasympathetic power, HP increases up to 50%. These changes occur during a time interval from 1 to 5 minutes.

In step 750 the current wakefulness level $W_c$ is compared with wakefulness signature level $W_s$.

Figure 8:
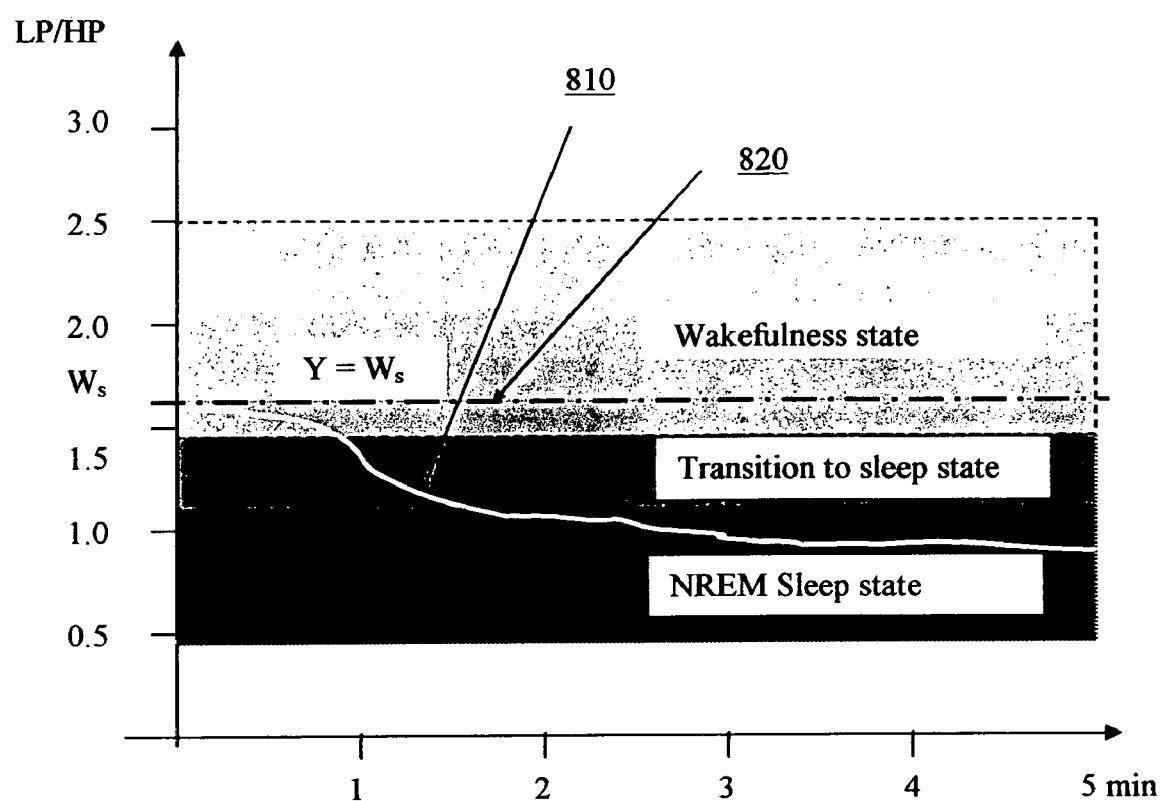
FIG. 8 illustrates an example of the drift of the user from the wakefulness stage to NREM sleep.

If $W_c \leq 0.75 * W_s$, (i.e. ratio of sympathetic activity to parasympathetic activity drops by equal or more then 25% during the last 5 minutes), then the user is considered in NREM sleep state. 25% drop is cited by all studies however, persons of ordinary skill in the art may successfully use other percent decrease. An example of the drift 810 of the user from wakefulness to sleep state is shown in FIG. 8. The ratio LP/HP dropped by more than 25% within less then 4 minutes. The line 820 shows the baseline of the wakefulness signature of the user.

If $W_c$ increases by more than 15% and LP doesn't change and the previous record shows that the user was in NREM stage, then the user is considered in REM sleep.

If $W_c$ increases by more than 15% and LP increases and the previous record shows that the user was in NREM or REM sleep, then the user is considered in the after-sleep wakefulness state.

Figure 9:
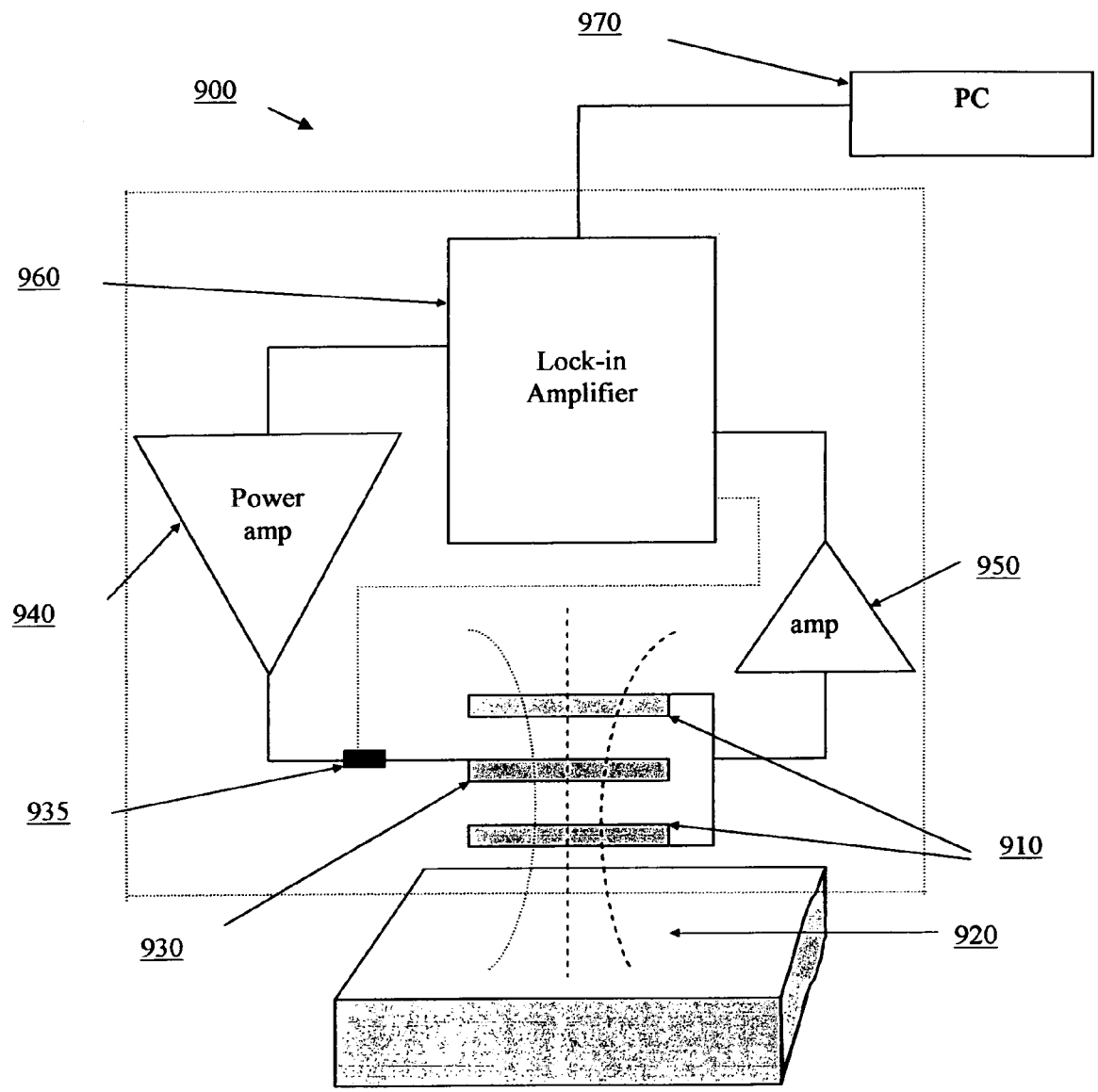
FIG. 9 is a block diagram of an exemplary embodiment of the electromagnetic inductance device for monitoring and evaluation of the sleep states of the user.

The exemplary device 900 shown on FIG. 9 comprises of 2 sensing coils 910 for supplying an induced current from the subject without contacting the body 920; excitation coil 930 for induction magnetic field into the subject; power amplifier 940 providing AC current to the excitation coil; amplifier 950 which serves for reducing an effect of residue voltage; lock-in amplifier 960 for driving the excitation coil; a PC 970 for controlling the lock-in amplifier, preprocessing of the digital data of CA waveforms, storing intermediate and sleep history data, calculations, graphic display and communication.

Sensing coils 910 are shielded in order to avoid capacitive effect and positioned from the excitation coil at approximately 5 mm. The distance from the excitation coil 930 to the body 920 should be approximately 20 mm.

The power amplifier 940 uses the oscillator signal from lock-in amplifier 960 to drive excitation coil 930. A commercial amplifier such as PA09, Apex Microtechnology with output current of 500 mA may be used as the power amplifier 940.

Since the measured signal is relatively small compared to the residual signal, an additional amplifier 950 is used before providing the signal to the lock-in amplifier for phase detection. The reference signal for phase detection is fed from the resistor 935. INA 106, Texas Instrument may be used as the amplifier 950.

The lock-in amplifier 960 provides oscillator output, phase detection and measurement of the output signal. A single-board lock-in amplifier LIA-BV-150, supplied by FEMTO and operating in a range of up to 150 kHz may be used in the present embodiment.

The PC 970, controls operation of the lock-in amplifier 960, hosts and run application FFT routine, provides evaluation of measured parameters, graphic display, and communication.

Figure 10:
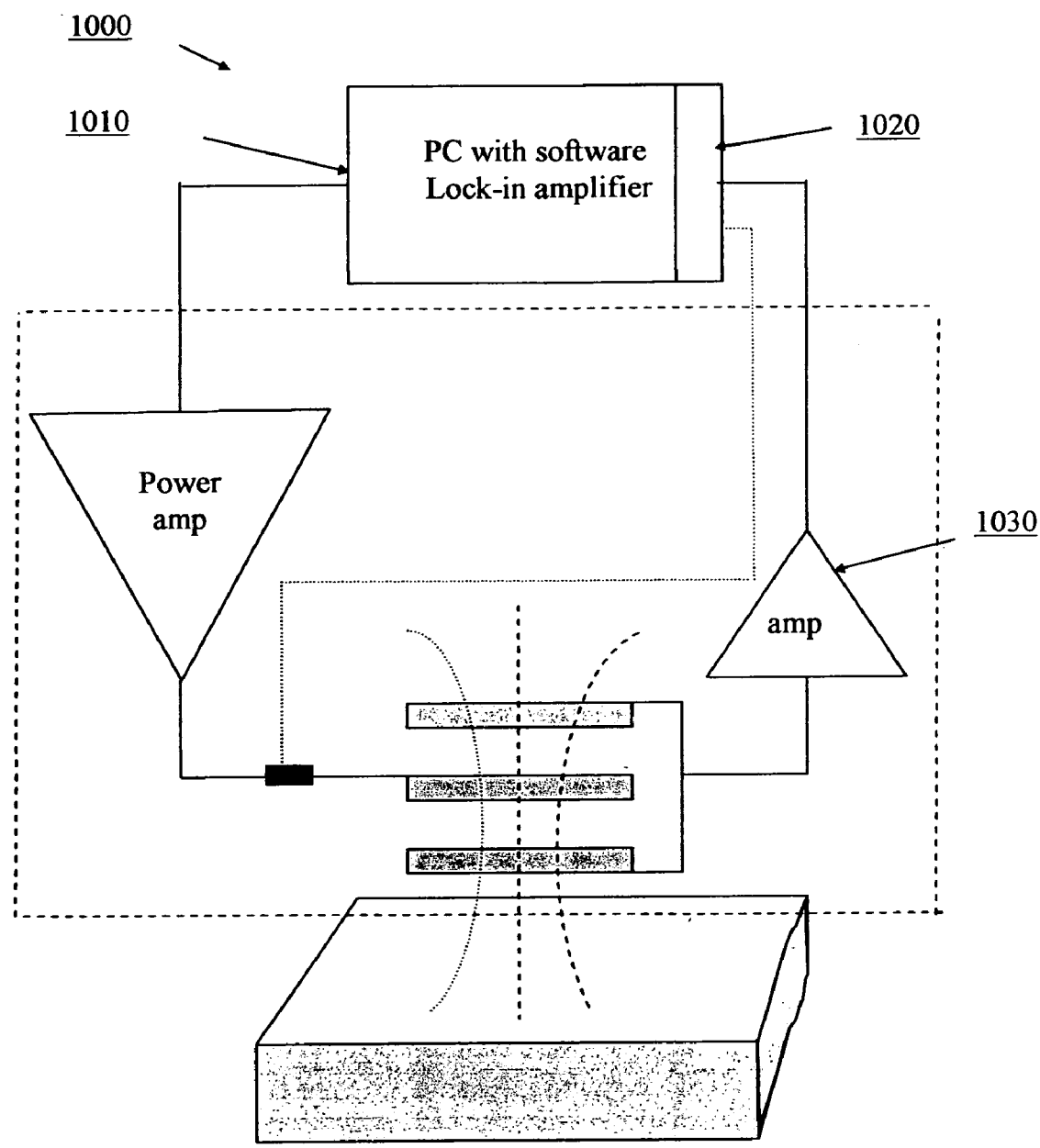
FIG. 10 is a block diagram of an exemplary embodiment of the electromagnetic inductance device for evaluation of fatigue utilizing a PC based lock-in amplifier.

FIG. 10 shows an example of the device 1000 utilizing PC based software lock-in amplifier 1010. A data acquisition board 1020 provides data exchange between the processor 1010 and amplifier 1030. A data acquisition board, PCI-MIO-16E-4, National Instrument may be successfully used. A PC based lock-in amplifier has significant advantages in terms of the cost, the size and flexibility. The device can be assembled in a single portable board. Software lock-in amplifier utilizing National Instrument, LabView v. 6.0.2 software may be used for this embodiment. Connection between the device and the PC may be also wireless utilizing Bluetooth, Wi-Fi or other RF technology.

What is claimed is:

1. A method for contactless monitoring and evaluation of sleep states of a user comprising:
   a) providing a contactless sleep monitoring device made in a form of a small mattress pad;
   b) providing an electromagnetic inductance device embedded into said small mattress pad and connected to a processor;
   c) passing an alternating current through an excitation coil;
   d) measuring and processing at least one induced current waveform associated with changes in eddy current losses in the torso region of the user which is derived from a receiver coil;
   e) determining sleep stages based on said changes in said eddy current.

2. The method of claim 1, wherein the act of processing said at least one induced current waveform comprises evaluation of a respiratory component and a cardiac activity component of said waveform.

3. The method of claim 2, wherein said respiratory component is smoothed using a cubic spline approximation method.

4. The method of claim 3, wherein said respiratory component is removed from said waveform to obtain said cardiac activity component.

5. The method of claim 2, wherein a duration of a cardiac cycle is determined using a width of a wave of said cardiac activity component, wherein the cardiac cycle is defined as:

$$HR_i = \frac{60}{W_i} * 1000$$

Where:
$HR_i$=heart rate of cardiac cycle i in beat/min;
$W_i$=width of wave i of said cardiac activity component in ms.

6. The method of claim 2, wherein a stroke volume is determined using a magnitude of a wave of said cardiac activity component and a cumulative cardiac activity index is determined using an area $Q_i$ below a wave of said cardiac activity component.

7. The method of claim 6, wherein said area $Q_i$ is determined by computing the integral of a wave of said cardiac activity component.

8. The method of claim 7, wherein the cardiac activity component signal is discrete and said area $Q_i$ is determined by computing the sum of the amplitudes of each sample within a wave of said cardiac activity component.

9. The method of claim 6, wherein said cumulative cardiac activity index is calculated as follows:

$$CA_i = k \times Q_i n.u.$$

Where:
k is a normalizing factor for converting the value of $Q_i$ into a meaningful value;
$Q_i$=area of wave i;
n.u. stands for normalized unit.

10. The method of claim 1, wherein power spectrum analysis is used for determining said sleep stages.

11. The method of claim 10, wherein a Fast Fourier Transform algorithm is applied for calculation of a low frequency activity, reflecting both sympathetic and parasympathetic activities, and a high frequency activity, reflecting parasympathetic activity.

12. The method of claim 11, wherein a total power, a low frequency activity power, and a high frequency activity power are calculated for the first 5 minutes of processing using said Fast Fourier Transform algorithm.

13. The method of claim 12, wherein in order to determine said sleep stages a current wakefulness level is compared with a wakefulness signature level.

14. The method of claim 13, wherein if said current wakefulness level is less than or equal to 75% of said wakefulness signature level, then the user is determined to be in a Non-Rapid Eye Movement sleep state.

15. The method of claim 13, wherein if said current wakefulness level increases by more than 15% and said low frequency activity power doesn't change and a previous record shows that the user was in a Non-Rapid Eye Movement stage, then the user is determined to be in a Rapid Eye Movement state.

16. The method of claim 13, wherein if said current wakefulness level increases by more than 15% and said low frequency activity power increases and a previous record shows that the user was in a Non-Rapid Eye Movement or Rapid Eye Movement sleep, then the user is determined to be in an after-sleep wakefulness state.

17. The method of claim 10, wherein a wakefulness signature level $W_s$ is calculated as follows:

$$W_s = \frac{LP_s}{HP_s}$$

Where:

$W_s$=wakefulness signature level;

$LP_s$=signature sympathetic activity power;

$HP_s$=signature parasympathetic activity power.

18. The method of claim 10, wherein a current wakefulness level $W_c$ is calculated in a 5 minute interval shifted by 30 seconds as follows:

$$W_c = \frac{LP_c}{HP_c}$$

Where:

$W_c$=current wakefulness level;

$LP_s$=current sympathetic activity power;

$HP_s$=current parasympathetic activity power.

19. A system for contactless monitoring and evaluation of sleep states of a user comprising:

a contactless sleep monitoring device made in a form of a small mattress pad;

an electromagnetic inductance device embedded into said small mattress pad and connected to a processor;

an excitation coil capable of inducing a magnetic field;

a sensing coil capable of acquiring signals representing changes of stroke volume and heart rate;

a power amplifier providing AC current to the excitation coil;

an amplifier capable of reducing an effect of residue voltage;

a lock-in amplifier for driving the excitation coil; and a personal computer for controlling the lock-in amplifier, preprocessing digital waveform data, storing intermediate and sleep history data, calculations, graphic display and communication;

wherein the personal computer is configured to process at least one induced current waveform derived from the sensing coil associated with changes in eddy current losses in the torso region of the user and determine sleep stages based on the changes in said eddy current.

20. The system of claim 19, wherein said excitation coil is made from flexible plastic-type material using metal lines and providing a strong and relatively uniform induction field.

* * * * *